US009237986B2

(12) United States Patent
Mansour et al.

(10) Patent No.: US 9,237,986 B2
(45) Date of Patent: Jan. 19, 2016

(54) VIAL ACCESS CAP AND SYRINGE WITH GRAVITY-ASSISTED VALVE

(71) Applicants: George Michel Mansour, Pomona, CA (US); Tyler Devin Panian, Long Beach, CA (US)

(72) Inventors: George Michel Mansour, Pomona, CA (US); Tyler Devin Panian, Long Beach, CA (US)

(73) Assignee: CareFusion 303, Inc., San Diego, CA (US)

(*) Notice: Subject to any disclaimer, the term of this patent is extended or adjusted under 35 U.S.C. 154(b) by 329 days.

(21) Appl. No.: 13/829,316

(22) Filed: Mar. 14, 2013

(65) Prior Publication Data

US 2014/0261876 A1 Sep. 18, 2014

(51) Int. Cl.

*A61J 1/20* (2006.01)
*A61M 5/28* (2006.01)
*A61J 1/14* (2006.01)

(52) U.S. Cl.

CPC *A61J 1/2096* (2013.01); *A61J 1/20* (2013.01); *A61M 5/28* (2013.01); *A61J 1/1412* (2013.01); *A61J 1/1418* (2015.05); *A61J 1/1487* (2015.05); *A61J 1/201* (2015.05); *A61J 1/2037* (2015.05)

(58) Field of Classification Search

CPC ......... A61J 1/1412; A61J 1/20; A61J 1/2096; A61J 2001/1487; A61J 2001/201; A61J 2001/2037; A81M 5/28

USPC .......................... 141/27, 301, 302, 319, 329; 604/411–416

See application file for complete search history.

(56) References Cited

U.S. PATENT DOCUMENTS 2,668,533 A * 2/1954 Evans .......................... 604/405
2,812,117 A * 11/1957 Butkus et al. ............ 222/189.09
2,954,769 A * 10/1960 Callahan et al. .............. 604/413
3,957,052 A * 5/1976 Topham ........................ 604/236
4,534,758 A * 8/1985 Akers et al. ..................... 604/85
4,576,594 A * 3/1986 Greenland .................... 604/251
4,857,068 A * 8/1989 Kahn ........................... 604/405
6,050,957 A * 4/2000 Desch .......................... 600/579
7,192,423 B2 * 3/2007 Wong ........................... 604/411
8,123,736 B2 2/2012 Kraushaar et al.

(Continued)

FOREIGN PATENT DOCUMENTS

WO WO-2013025946 A1 2/2013

OTHER PUBLICATIONS

International Search Report and Written Opinion for International Application No. PCT/US2014/019630, dated Jun. 26, 2014, 12 pages.

(Continued)

*Primary Examiner* — Timothy L Maust
(74) *Attorney, Agent, or Firm* — McDermott Will & Emery

(57) ABSTRACT

Systems and apparatus for providing fluid communications are described. In an example, a vial access cap includes a connector having an opening for providing access to a fluid pathway; a canella extending into an interior of a vial, the canella having a fluid lumen operatively coupled to the fluid pathway and a gas lumen; and a gravity-assisted valve comprising a valve body defining an elongated valve cavity, a first port, a second port operatively coupled to the gas lumen, and a valve member movable between a sealable end of the elongated valve cavity proximal to the first port and a non-sealable end of the elongated valve cavity proximal to the second port. In other examples, a syringe including a gravity-assisted valve and a system including gravity-assisted valves are described.

19 Claims, 7 Drawing Sheets

(56) References Cited

U.S. PATENT DOCUMENTS

| | | | | |
|---|---|---|---|---|
| 8,506,548 | B2 * | 8/2013 | Okiyama | 604/406 |
| 8,821,436 | B2 * | 9/2014 | Mosler et al. | 604/82 |
| 2009/0254031 | A1 | 10/2009 | Lee | |
| 2010/0204071 | A1 | 8/2010 | Kraushaar et al. | |
| 2010/0276034 | A1 | 11/2010 | Gonnelli et al. | |
| 2011/0062703 | A1 | 3/2011 | Lopez et al. | |
| 2011/0208128 | A1 | 8/2011 | Wu et al. | |
| 2015/0000787 | A1 * | 1/2015 | Fangrow | 141/319 |

OTHER PUBLICATIONS

International Preliminary Examining Authority Written Opinion for International Application No. PCT/US2014/019630, dated Mar. 31, 2015, 7 pages.

* cited by examiner

VIAL ACCESS CAP AND SYRINGE WITH GRAVITY-ASSISTED VALVE

CROSS-REFERENCES TO RELATED APPLICATIONS

Not applicable.

BACKGROUND

1. Field

The present disclosure generally relates to vials and syringes, and, in particular, to vial access systems and apparatus.

2. Description of the Related Art

Medications and similarly dispensed substances are typically stored in a vial that is sealed with a vial cap having an access port for injecting fluid into or removing fluid from the vial. A closure of the vial usually include a pierceable rubber stopper formed of an elastomeric material such as butyl rubber or the like. The vial cap, typically formed of metal, is crimped over the pierceable rubber stopper and a flange of the vial to hold the stopper in place in the opening of the vial. The vial cap has an opening, or access port, through which the stopper and the vial opening may be accessed. A sharp cannula, such as a needle, or the piercing end of a vial adapter is typically inserted into the access port of a vial cap to make fluid connection with the contents of a vial.

Some medications for administration, such as many types of chemotherapy preparations, are packaged and shipped in a concentrated or dehydrated form, such as, but not limited to, a concentrated liquid or a dehydrated powder. Before these dehydrated or concentrated medicaments can be administered to patients, the medicaments must be reconstituted by adding a liquid rehydration or dilution component or constituent to the concentrated or dehydrated medicament. Gases from the reconstitution process, particularly for some chemotherapy preparations, can be toxic and require a closed or non-vented arrangement during processing and administration.

SUMMARY

In certain embodiments, a vial access cap is disclosed that comprises a connector having an opening for providing access to a fluid pathway; a canella extending into an interior of a vial, the canella having a fluid lumen operatively coupled to the fluid pathway and a gas lumen; and a gravity-assisted valve comprising a valve body defining an elongated valve cavity, a first port, a second port operatively coupled to the gas lumen, and a valve member movable between a sealable end of the elongated valve cavity proximal to the first port and a non-sealable end of the elongated valve cavity proximal to the second port.

In certain embodiments, a syringe is disclosed that comprises a connector body section defining a longitudinal axis and comprising, a tip portion for fluid ingress and egress; and a gravity-assisted valve comprising a valve body defining an elongated valve cavity generally aligned with the longitudinal axis, a first port operatively coupled to the tip portion, a second port, and a valve member movable between a sealable end of the elongated valve cavity proximal to the first port and a non-sealable end of the elongated valve cavity proximal to the second port; and a barrel section generally aligned with the longitudinal axis and slidably engaged with a plunger, the barrel section defining a fluid reservoir within a volume of the barrel section controllable by an end of the plunger proximal the connector body section, the fluid reservoir operatively coupled to the second port of the gravity-assisted valve.

In certain embodiments, a system is disclosed that comprises a vial access cap affixed to a vial, the vial access cap comprising, a connector having an opening for providing access to a fluid pathway and sealable access to a gas pathway; a canella extending into an interior of a vial, the canella having a fluid lumen operatively coupled to the fluid pathway and a gas lumen; and a first gravity-assisted valve comprising a first valve body defining a first elongated valve cavity, a first port of the first gravity-assisted valve operatively coupled to the gas pathway, a second port of the first gravity-assisted valve operatively coupled to the gas lumen, and a first valve member movable between a sealable end of the first elongated valve cavity proximal to the first port of the first gravity-assisted valve and a non-sealable end of the first elongated valve cavity proximal to the second port of the first gravity-assisted valve; and a syringe comprising, a connector body section defining a longitudinal axis and comprising, a tip portion for fluid ingress and egress; and a second gravity-assisted valve comprising a second valve body defining a second elongated valve cavity generally aligned with the longitudinal axis, a first port of the second gravity-assisted valve operatively coupled to the tip portion, a second port of the second gravity-assisted valve, and a second valve member movable between a sealable end of the second elongated valve cavity proximal to the first port of the second gravity-assisted valve and a non-sealable end of the second elongated valve cavity proximal to the second port of the second gravity-assisted valve; and a barrel section generally aligned with the longitudinal axis and slidably engaged with a plunger, the barrel section defining a fluid reservoir within a volume of the barrel section controllable by an end of the plunger proximal the connector body section, the fluid reservoir operatively coupled to the second port of the second gravity-assisted valve. The tip portion of the syringe is removably coupled to the opening of the vial access cap. The fluid pathway and the gas pathway of the vial access cap are operatively coupled to a fluid pathway and a gas pathway of the syringe.

It is understood that various configurations of the subject technology will become readily apparent to those skilled in the art from the disclosure, wherein various configurations of the subject technology are shown and described by way of illustration. As will be realized, the subject technology is capable of other and different configurations and its several details are capable of modification in various other respects, all without departing from the scope of the subject technology. Accordingly, the summary, drawings and detailed description are to be regarded as illustrative in nature and not as restrictive.

BRIEF DESCRIPTION OF THE DRAWINGS

The accompanying drawings, which are included to provide further understanding and are incorporated in and constitute a part of this specification, illustrate disclosed embodiments and together with the description serve to explain the principles of the disclosed embodiments. In the drawings.

DETAILED DESCRIPTION

The detailed description set forth below is intended as a description of various configurations of the subject technology and is not intended to represent the only configurations in which the subject technology may be practiced. The detailed description includes specific details for the purpose of providing a thorough understanding of the subject technology. However, it will be apparent to those skilled in the art that the subject technology may be practiced without these specific details. In some instances, well-known structures and components are shown in block diagram form in order to avoid obscuring the concepts of the subject technology. Like components are labeled with identical element numbers for ease of understanding. Reference numbers may have letter suffixes appended to indicate separate instances of a common element while being referred to generically by the same number without a suffix letter.

While the following description is directed to the administration of medical fluid to a patient by a medical practitioner using the disclosed vial access caps and syringes, it is to be understood that this description is only an example of usage and does not limit the scope of the claims. Various aspects of the disclosed vial access caps and syringes may be used in any application where it is desirable to control fluid pathways into and out of a container.

Whether reconstituting a medicament or removing medication from a vial for administration, it is advantageous to provide vented and non-vented arrangements that ensure no breaches of the system contaminate the medication or expel toxic gases into the ambient environment.

Certain disclosed embodiments of vial access caps, syringes, and systems for fluid communications having vial access caps and syringes incorporating one or more exemplary gravity-assisted valves help ensure that no breaches occur and proper fluid communications are maintained during the preparation of medications in various vented and non-vented arrangements and the subsequent administration of the medications.

Figure 1B:
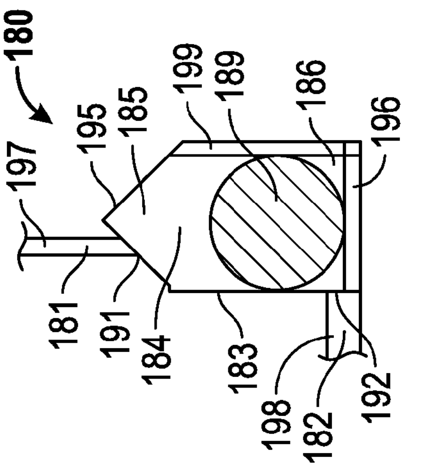
FIG. 1B is an enlarged, longitudinal cross-sectional view illustrating an example of a gravity-assisted valve of an vial access cap, in accordance with various aspects of the present disclosure.
Figure 1A:
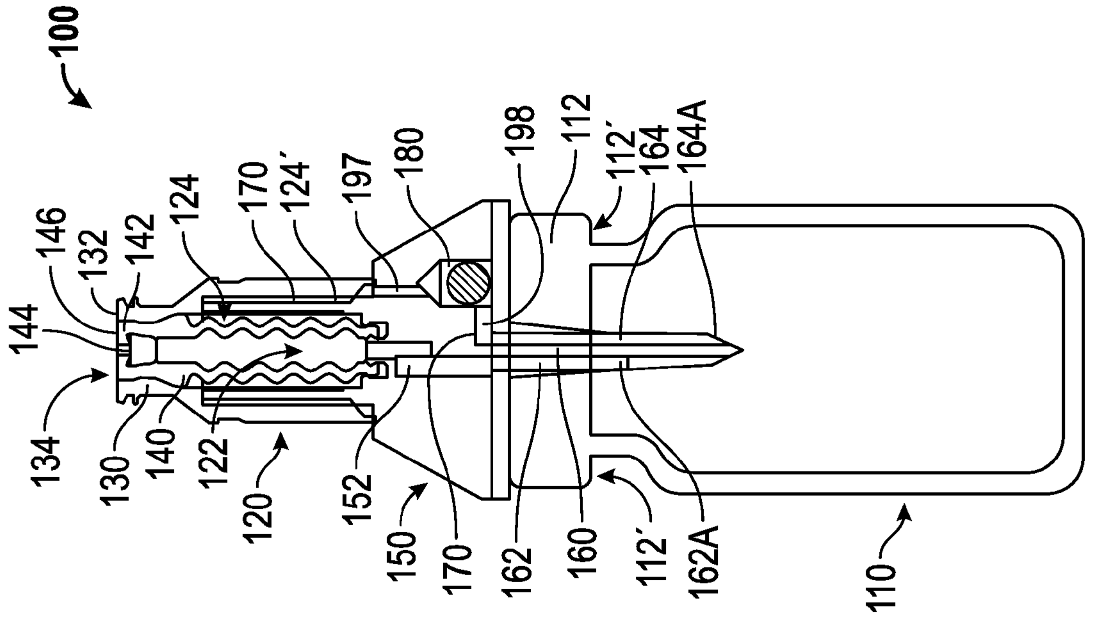
FIG. 1A is a longitudinal cross-sectional view illustrating an example of a vial access cap, in accordance with various aspects of the present disclosure.

FIG. 1A illustrates an exemplary vial access cap 100 in accordance with certain embodiments. The vial access cap 100 is shown coupled to a vial 110 and comprises a connector 120, a base 150 including a gravity-assisted valve 180, and a canella 160. Connector 120 is a needleless connector having an opening 134 adapted to a female luer fitting in accordance with certain embodiments. However, it is understood that some embodiments of the connector 120 do not have a luer tapered fitting. The connector 120 includes a body section 130 with a top surface 132 of the opening 134.

In certain embodiments, a collapsible valve 140 is disposed within the body section 130 and has a valve tip 142 that is disposed within the opening 134 such that a valve face 146 is approximately flush with the top surface 132 of the body section 130. The valve tip 142 comprises a slit 144 that is forced closed when the valve tip 142 is positioned in a closed configuration (as illustrated in FIG. 1A). The slit 144 will self-open when the collapsible valve 140 is compressed and the valve face 146 is displaced, by a male luer tip for example, into a wider cavity 124 of the body section 130. The slit 144 provides access to an internal pathway 122 of the collapsible valve 140. The internal pathway 122 is operatively coupled to a fluid line 152 in the base 150. In some embodiments, cavity 124 provides an interstitial space defining a gas pathway for venting or adding a gas (e.g., sterilized air) through the base 150 and into the vial 110.

Canella 160 extends into the vial 110 and is operatively coupled to the base 150. In some embodiments, canella 160 includes a fluid lumen 162 generally used for the flow of medication or diluent and a gas lumen 164 generally used for the flow of sterilized air and/or aerosolized contents discharged during the process of reconstituting a medicament. It is to be understood that the gas lumen 164 may be used in venting and non-venting arrangements. In some embodiments, an aperture 162*a* of the fluid lumen 162 is disposed on the canella 160 proximal to the vial rim 112 and an aperture 164*a* of the gas lumen 162 is disposed on the canella 160 distal to the vial rim 112.

FIG. 1B provides an enlarged, longitudinal cross-sectional view of the exemplary gravity-assisted valve 180 in accordance with certain embodiments. Gravity-assisted valve 180 comprises a valve body 183 defining an elongated valve cavity 184 having generally cylindrical and conical sections. Valve 180 comprises a first port 181 proximal to a sealable end 185 having a generally smooth, ramped or conical interior wall 195 of the valve cavity 184, and a second port 192 proximal to a non-sealable end 186 having a ribbed or channelized non-sealable interior wall portion 196 (e.g., a bottom of the valve body 183 having a generally circular cross-sectional area). A valve member 189 is disposed within the elongated valve cavity 184 and movable between the sealable end 185 and non-sealable end 186. In accordance with certain embodiments, the valve member is a substantially spherical element, such as, but not limited to, a ball bearing comprising a non-reactive material with respect to the type of fluid communication for which it is to be engaged covering at least an outer surface of the ball bearing.

In certain embodiments, a ribbed or channelized longitudinal interior wall portion 199 extends along at least a portion of the generally cylindrical section of the elongated valve cavity 184. The longitudinal interior wall portion 199 generally extends from the ribbed non-sealable interior wall portion 196 to proximal the generally smooth, ramped or conical interior wall 195 of the sealable end 185. The ribs or channels along the interior longitudinal interior wall portion 199 and the interior wall portion 196 proximal the non-sealable end 186 provide a gas pathway when the valve member 189 resides in the elongated valve cavity 184 proximal to the non-sealable end 186.

The first port 181 includes a first port aperture 191 disposed on the ramped or conical interior wall 195 such that the valve member 189 will seal or block flow through the aperture 191 when the valve member 189 is in a first position proximal to the sealable end 185. The first port 181 also includes a first port conduit 197 extending to a portion of the cavity 124' of the connector 110. The second port 182 includes a lateral second port conduit 198 and a second port aperture 192 disposed on the generally cylindrical section of the elongated valve cavity 184 proximal the ribbed non-sealable interior wall portion 196 such that the valve member 189 cannot seal or block flow through the aperture 192 when the valve member 189 is in a second position proximal to the non-sealable end 186.

In accordance with certain embodiments described above and illustrated in FIGS. 1A and 1B, vial access cap 100 and vial 110 are combined to provide an integrated vial design solution that drug compounders can use to encase medications for distribution to hospitals and pharmacies or the like. For example, a thin aluminum cover (not shown) or similar material encloses the vial access cap 100 (leaving access to the opening 134) and is crimped securely to the underside 112' of the vial rim 112. In this regard, the integrated vial design of the present disclosure eliminates the need for spikes, thereby reducing costs and increasing operational efficiencies for the drug administration entities. However, in some embodiments, the vial access cap 100 or various aspects thereof may be incorporated into a vial adapter for piercing the septum of a vial to obtain access to the medication therein.

In certain embodiments, one or more filters 170 are disposed at various locations along a gas pathway, for example, in the first port conduit 197 or in a portion of the cavity 124' of the connector 120. The filters 170 include a thin membrane or thickness of porous material, such as, but not limited to, polytetrafluoroethylene (PTFE) or other vinyl polymers having various pore sizes in some implementations.

Figure 2A:
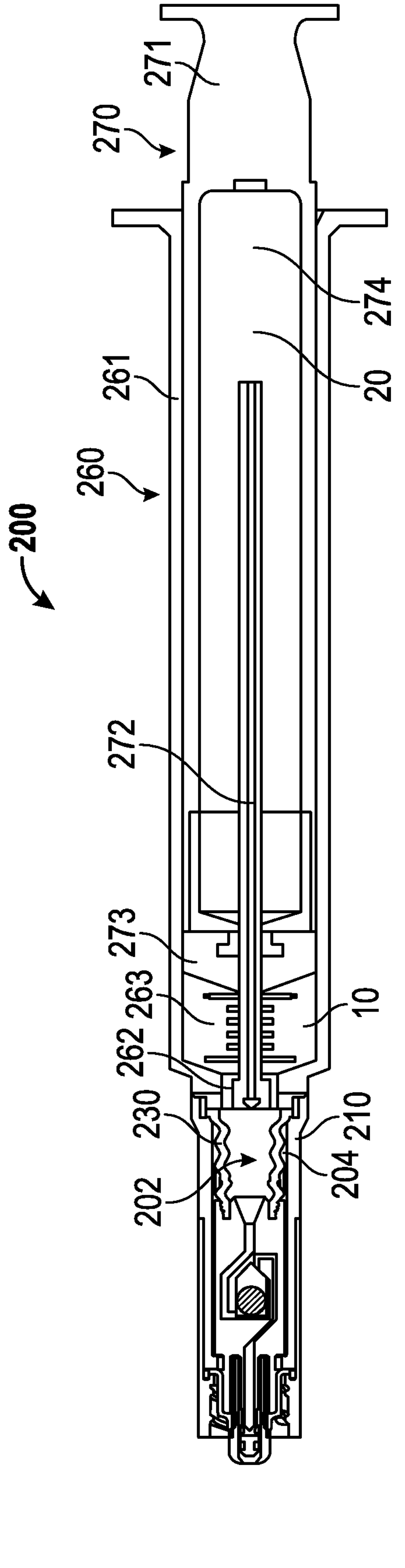
FIG. 2A is a cross-sectional view illustrating an example of a syringe, in accordance with aspects of the present disclosure.
Figure 2C:
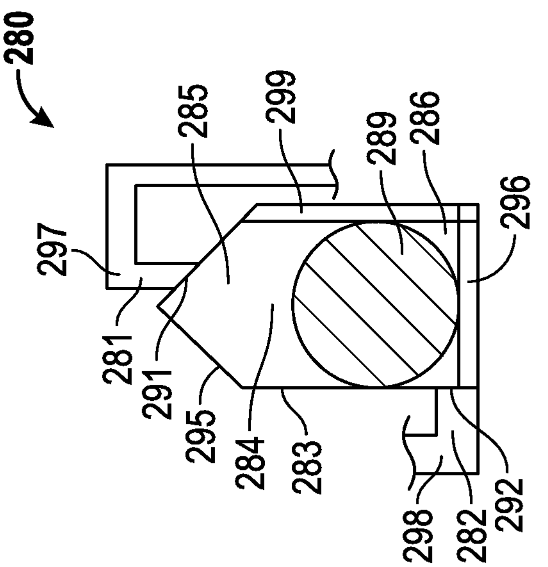
FIG. 2C is an enlarged, longitudinal cross-sectional view illustrating an example of a gravity-assisted valve of a syringe, in accordance with aspects of the present disclosure.
Figure 2B:
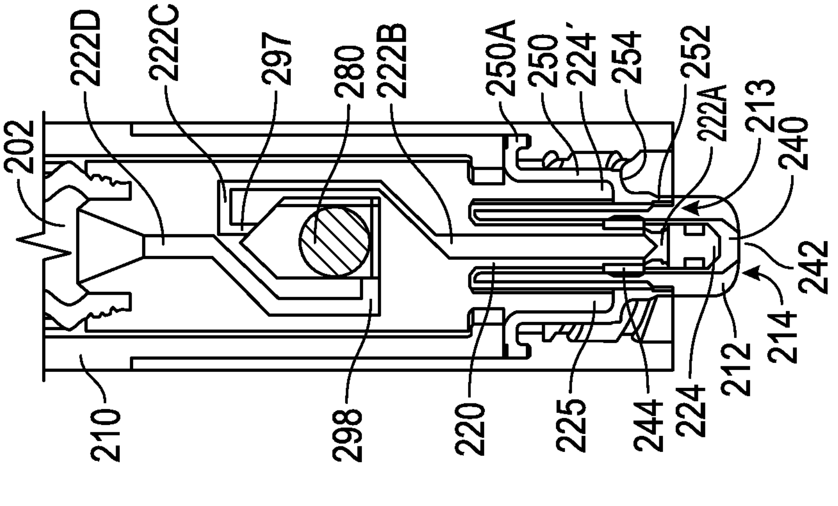
FIG. 2B is an enlarged, longitudinal cross-sectional view illustrating an example of a section of a syringe, in accordance with aspects of the present disclosure.

FIGS. 2A and 2B illustrate an exemplary syringe 200 in accordance with certain embodiments. Syringe 200 comprises a connector body 210, a barrel 260 having a barrel tube 261, a plunger 270 having a plunger tube 271 and an interior volume 274 defining a gas reservoir, for example, a balloon (not shown) in a non-vented arrangement, or a filter (not shown) in a vented arrangement. A sealing member 273 of plunger 270, in conjunction with barrel tube 261, defines a fluid reservoir 263 and directs the flow of medication 10 (or diluent) into or out of the syringe 200. A fluid channel 262 provides a passage from the fluid reservoir 263 to the connector body 210 and a gas channel 272 provides a passage from the interior volume 274 to the connector body 210.

As shown in the enlarged, longitudinal cross-sectional view of FIG. 2B, the connector body 210 of the syringe 200 has a male tip or fitting 212 with a syringe port 214. In certain embodiments, the male tip (or fitting) 212 does not have a luer taper, and therefore may provide for a gas pathway to accommodate certain venting and non-venting arrangements. A valve 220 is slidably disposed within the body 210 and partially within the male tip 212. A sealing tip 240 is disposed over a tip 224 of the valve 220. The valve 220 includes accordion bellows 230 disposed within cavity 204 distal to the valve 220. The sealing tip 240 sealingly contacts the port 214 of the male tip 212 such that the external surface 242 of the sealing tip 240 is approximately flush with the external surface of the male tip 212 around the syringe port 214. The sealing tip 240 includes a second seal 244 that forms a sliding seal between the valve 220 and the male tip 212.

A fluid pathway 222 of the connector body 210 passes through the valve 220 and the sealing tip 240. In certain embodiments, the fluid pathway 222 incorporates a gravity-assisted valve 280, and comprises a longitudinal fluid pathway portion 222*d* that passes from the open internal cavity 202 of the bellows 230 to a lateral second port conduit 298 of the gravity-assisted valve 280, through the gravity-assisted valve 280 to a longitudinal first port conduit 297 (having a flow direction opposite that of the longitudinal fluid pathway portion 222*d*). The fluid pathway 222 then extends from the longitudinal first port conduit 297 of the gravity-assisted valve 280 to a lateral fluid pathway portion 222*c*, from the lateral fluid pathway portion 222*c* to a longitudinal fluid pathway portion 222*b*, and from the longitudinal fluid pathway portion 222*b* to a lateral fluid pathway portion 122*a* that is open to the interior of the male tip or fitting 212. The internal cavity 202 of the connector body 210 fluidly connects to the fluid channel 262 and fluid reservoir 263.

The valve 220 includes a plurality of fingers 225 that extend toward the tip 224 of the valve 220. A sliding seal 250 is disposed over a portion of the male tip 212 and the fingers 225 with a tip 252 of the sliding seal 250 in sealing contact with a recess 213 in the male fitting 212. An end 250*a* of the sliding seal 250 distal to the male tip 212 is captured and secured, in accordance with some embodiments, between two components that form the connector body 210. The sliding seal 250 also has a shoulder 254 disposed proximal to the tips 224' of the fingers 124. In certain embodiments, the sliding seal 250 comprises a flexible material, such as, but not limited to, and elastomeric material.

In certain embodiments, the gravity-assisted valve 280 of the syringe 200 is similar to the valve 180 shown in FIG. 2B, except that the gravity-assisted valve 280 in the syringe 200 is in the fluid path and the gravity-assisted valve 180 in the vial access cap 100 is in the gas path. In some embodiments, the gravity-assisted valve 280 of the syringe 200 is placed in other portions of the fluid pathway (e.g., fluid pathway 222) and may increase the diameter or cross-sectional area for that longitudinal portion of the syringe body (e.g., connector body 210). In other embodiments, the gravity-assisted valve 280 is an adapter or connector apparatus that is connected in series with the syringe 280 as an extension of the male tip and port assembly (e.g., syringe port 214 and male tip 212).

Also, it is pertinent to note the difference in conduit directions entering the first and second ports 181, 182 of the vial access gravity-assisted valve 180 and the first and second ports 281, 282 of the syringe gravity-assisted valve 280. These directional aspects with respect to the gravity-assisted valves 180, 280 have a bearing on their operation as described below with respect to FIGS. 3, 4A-D, 5, and 6A-D.

Figure 3:
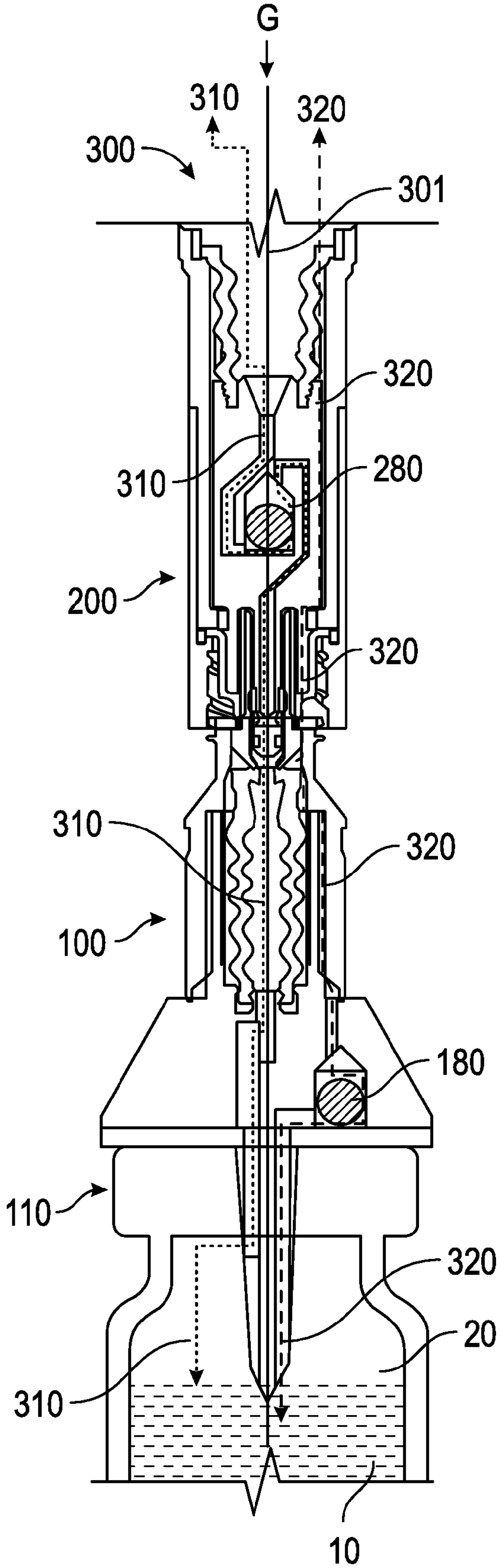
FIG. 3 is a cross-sectional view illustrating an example of a system for fluid communication having a vial access cap and a syringe in an upright orientation, in accordance with aspects of the present disclosure.

FIG. 3 illustrates a cross-sectional view of a system 300 for fluid communication having a vial access cap 100 and a syringe 200 in an upright orientation. In certain embodiments, the vial access cap 100 is connected to a vial 110 having fluid 10 (e.g., a medication or diluent) and gas 20 therein, and the syringe 200 is operatively coupled to the vial access cap 100. A longitudinal axis 301 is defined for the system 300 showing the alignment of the gravity-assisted valves 180, 280 with respect to gravity (G). In the upright orientation, a vial's bottom surface (not shown) is proximal to the ground and the plunger 270 of the syringe 200 is distal to the ground in a generally longitudinal arrangement.

A fluid flow path 310 extends from the vial 100 through the fluid lumen 162 to the fluid reservoir 263 of the syringe 200 (e.g., through the various pathways, conduits, and channels described and illustrated in FIGS. 1A, 1B, 2A, 2B, and 2C. A gas flow path 320 extends from the vial 100 through the gas lumen 164 to the interior volume 274 of the plunger 270 of the syringe 200 (e.g., through the various pathways, conduits, and channels described and illustrated in FIGS. 1A, 1B, 2A, 2B, and 2C.

In the upright orientation, a diluent from the fluid reservoir 263 of the syringe 200 may be added to the vial 110 to reconstitute a medicament therein. Gases from the reconstitution process, particularly for some chemotherapy preparations, can be toxic and require a closed or non-vented arrangement during processing and administration of such medication. Additionally, in some non-vented arrangements, a sterilized air may be added to the vial 110 to either increase the pressure in the vial 110 to facilitate more efficient fluid flow or bring the vial 110 to a neutral or equalized pressure without contaminating the medications therein. One or more exemplary gravity-assisted valves 180, 280 incorporated into a vial access cap 100, a syringe 200, or a system having a vial access cap 100 and a syringe 200 help ensure that no breaches occur and proper fluid communications are maintained during the preparation of medications in various non-vented arrangements and vented arrangements.

FIGS. 4A-4D illustrate positions of the gravity-assisted valves 180, 280 of the syringe 200 and vial access cap 100 during various operations when in the upright orientation shown in FIG. 3. It is understood that, in certain embodiments, each of the valve members 189, 289 has a weight sufficient to counteract hydrostatic pressure from a gas or fluid in system 300. In general, an injection, expulsion, or suction force (or other applied or resulting force) applied to either the fluid flow path or gas flow path 320 upon the valve member 189, 289 or movement of the apparatus utilizing the gravity-assisted valve 180, 280 is required to move the valve member 189, 289 from one position to another.

In this regard, the gravity-assisted valve 180, 280 comprises at least two positions interrelated with the various operations and orientations of the system 300 in accordance with certain embodiments. For example, in a first position, the valve member 189, 289 is proximal to the sealable end 185, 285 such that the gravity-assisted valve 180, 280 is sealed at the first port 181, 281. In a second position, the valve member 189, 289 is proximal to the non-sealable end 186, 286 such that the gravity-assisted valve 180, 280 is not sealed at the first port 181, 281 and a gas or fluid can flow through the valve 180, 280.

Additionally, in the upright orientation, the gravity-assisted valves 180, 280 are biased in the second position. When biased in the second position, the gravity-assisted valves 180, 280 remain in the second position in accordance with certain aspects.

Figure 4A:
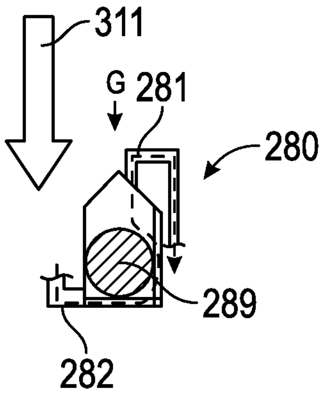
FIGS. 4A-4D are longitudinal cross-sectional views illustrating exemplary embodiments of gravity-assisted valves of a syringe and a vial access cap in an upright orientation, in accordance with aspects of the present disclosure.
Figure 4B:
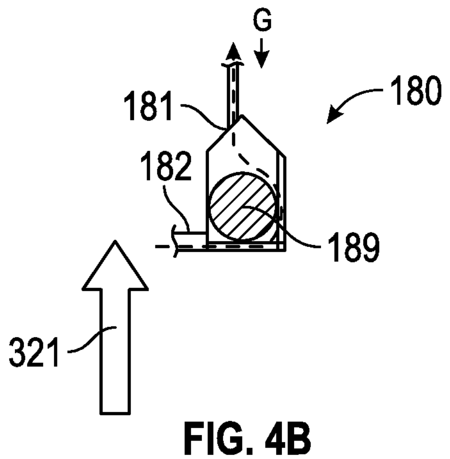

Referring to FIG. 4A, when an injection force 311 is applied to the fluid flow path 310 (e.g., the plunger 270 is pushed into the barrel tube 261) while in the upright orientation, the gravity-assisted valve 280 will remain in the second position and the fluid 10 will flow from the second port 282 around the valve member 289 and out of the first port 281 in accordance with certain embodiments. Consequently, as shown in FIG. 4B, when fluid 10 reaches the vial 110, an expulsion force 321 is exerted to the gas flow path 320 caused by an increase in the volume of fluid 10 (e.g., medication or diluent) entering the vial 110 or a reaction of the medicaments. As gas 20 exits the vial 110, the gravity-assisted valve 180 will remain in the second position and gas 20 will flow from the second port 182 around the valve member 189 and out of the first port 181 in accordance with certain embodiments.

Figure 4C:
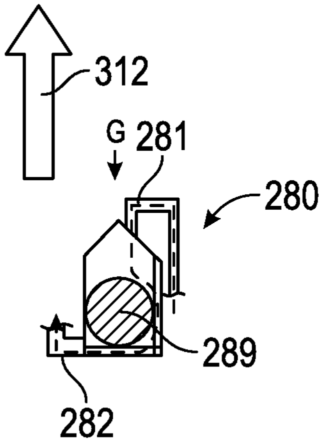
Figure 4D:
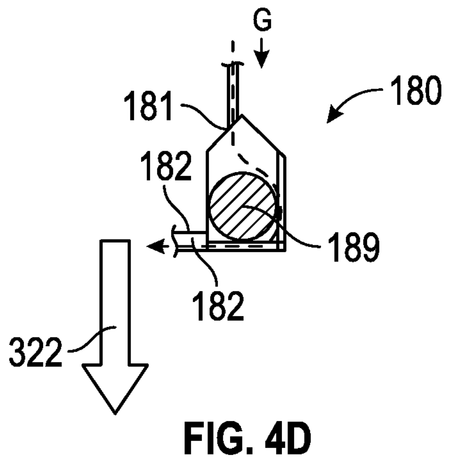

In FIG. 4C, when a suction force 312 is applied to the fluid flow path 310 (e.g., the plunger 270 is pulled away from the barrel tube 261) while in the upright orientation, the gravity-assisted valve 280 will remain in the second position and the fluid 10 will flow from the first port 281 around the valve member 289 and out of the second port 282 in accordance with certain embodiments. Consequently, as shown in FIG. 4D, when fluid 10 is removed from the vial 110, a suction force 322 is applied to on the gas flow path 320 due to a reduction of volume of fluid 10 in the vial 110. As gas 20 enters the vial 110, the gravity-assisted valve 180 will remain in the second position and gas 20 will flow from the first port 181 around the valve member 189 and out of the second port 182 in accordance with certain embodiments. A similar operation of the gravity-assisted valve 180 as illustrated in FIG. 4D will result when a gas 20 is expelled from the interior volume 274 of the plunger 270 (e.g., sterilized air) though the gas flow path 320.

Figure 5:
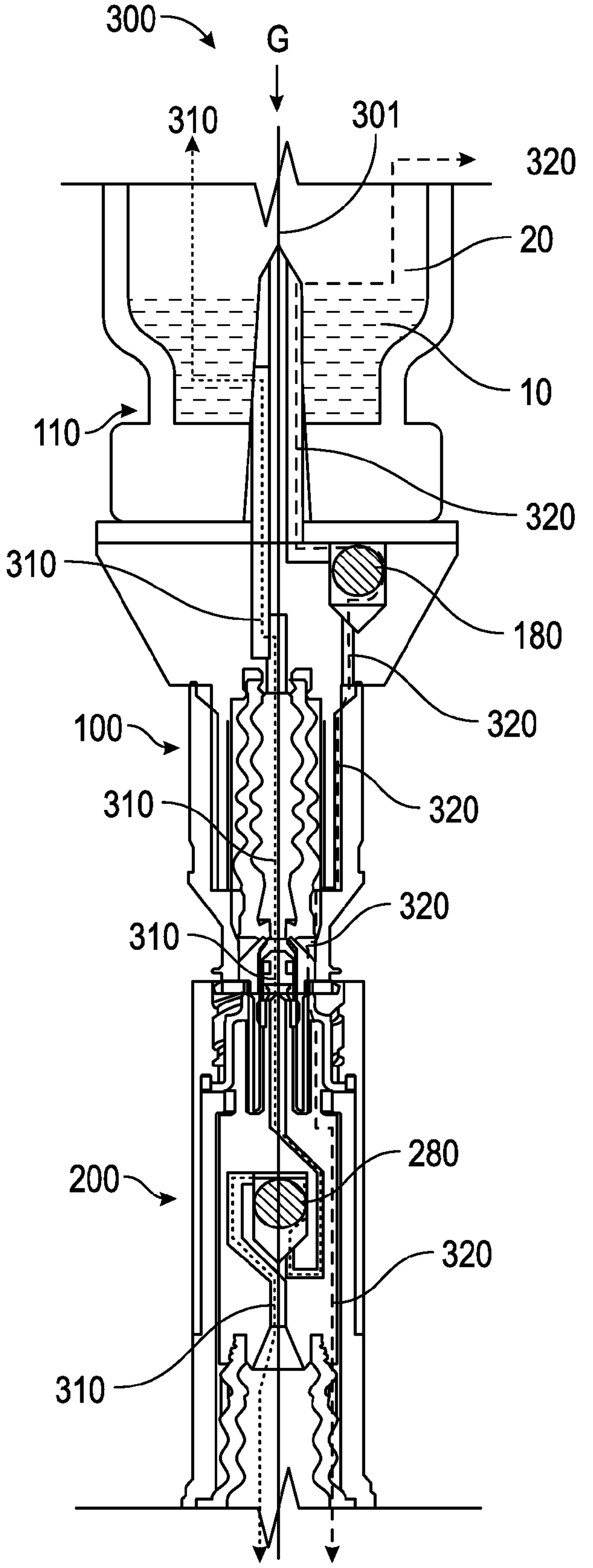
FIG. 5 is a cross-sectional view illustrating an example of a system for fluid communication having a vial access cap and a syringe in an inverted orientation, in accordance with aspects of the present disclosure.

FIG. 5 illustrates the system 300 in an inverted orientation in which the vial access cap 100 faces downwardly and is fluidly connected to the syringe 200 having its plunger 270 proximal to the ground, in accordance with certain embodiments. The inverted orientation provides an efficient manner in which medication from the vial 110 is accessed and transferred to a syringe 200, but the release of gas or fluid into the ambient environment can be hazardous and must be avoided in certain medication preparation and administration.

FIGS. 6A-6D illustrate positions of the gravity-assisted valves 180, 280 of the syringe 200 and vial access cap 100 during various operations when in the inverted orientation shown in FIG. 5.

In the inverted orientation, the gravity-assisted valves 180, 280 are biased in the first position. In other words, the valve member 189, 289 is proximal to the sealable end 185, 285 such that the gravity-assisted valve 180, 280 is sealed at the first port 181, 281. When biased in the first position, the gravity-assisted valves 180, 280 may be compelled to move to the second position.

Figure 6A:
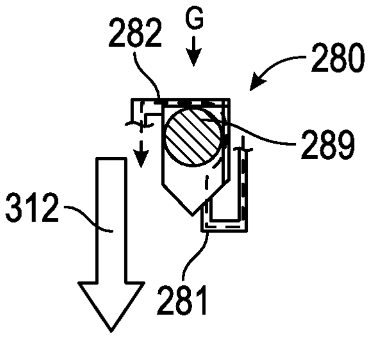
FIGS. 6A-6D are longitudinal cross-sectional views illustrating exemplary embodiments of gravity-assisted valves of a syringe and a vial access cap in an inverted orientation, in accordance with aspects of the present disclosure.

Referring now to FIG. 6A, when a suction force 312 is applied to the fluid flow path 310 (e.g., the plunger 270 is pulled away from the barrel tube 261) while in the inverted orientation, the gravity-assisted valve 280 will move from the first position to the second position and the fluid 10 will flow from the first port 281 providing fluid pressure to the valve member 289 in opposition of gravity, and the fluid 10 will then flow around the valve member 289 and out of the second port 282 and into the fluid reservoir 263 in accordance with certain embodiments. In some embodiments as illustrated in FIGS. 2C and 6A, the second port aperture 292 may abut or extend into the ribbed non-sealable interior wall portion 296 so that the valve member 289 cannot fully obstruct the second port aperture 292, and the ribs or channels of the longitudinal interior wall portion 299 are arranged on a wall portion generally opposite the second port aperture 292. Hence, the resulting fluid flow extends around a longitudinally top area of the elongated valve cavity 284 and does not intersect and impede the valve member's return path to the first position into the sealable end 185 of the elongated valve cavity 284.

Figure 6B:
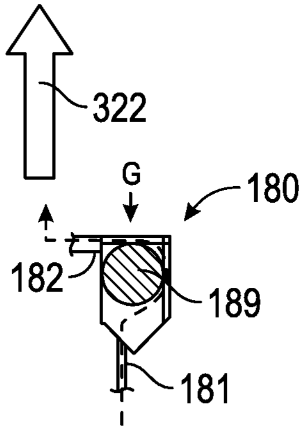

With reference to FIG. 6B, when fluid 10 is removed from the vial 110, a suction force 322 is applied to the gas flow path 320 due to a reduction of volume of fluid 10 in the vial 110. When the suction force 322 reaches a threshold, gas 20 will be forced to enter the vial 110, thereby causing the gravity-assisted valve 180 to move from the first position to the second position. Gas 20 will flow from the first port 181 providing gas pressure to the valve member 189 in opposition of gravity, and the gas 20 will then flow around the valve member 189 and out of the second port 282 and into the vial 110 in accordance with certain embodiments.

Figure 6C:
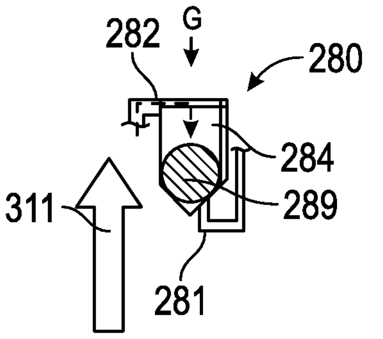

In FIG. 6C, when an injection force 311 is applied to the fluid flow path 310 (e.g., the plunger 270 is pushed into the barrel tube 261) while in the inverted orientation, the gravity-assisted valve 280 will move from the second position to the first position due to the removal of the suction force from the second port 282, the gravitational force of the valve member 289, and the injection force of the fluid 10 newly provided from the plunger 270 to the second port 282. When the gravity-assisted valve 280 is in the first position, the first port 281 will be blocked and the fluid 10 will accumulate in the elongated valve cavity and be immediately prevented from passing through fluid flow path 310 into the vial 110. Due to the proximity of the gravity-assisted valve 280 to the fluid pressure source (i.e., the injection force from the plunger 270), there is no fluid pressure build-up throughout the entire system 300 that could cause the breach of a valve, seal, conduit, or other component of the system 300 that may otherwise fail due to the pressure caused by an injection force from the plunger 270 that is not constrained.

Figure 6D:
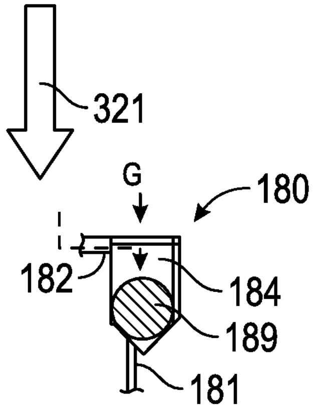

Consequently, as shown in FIG. 6D, when fluid 10 ceases to be removed from the vial 110, the suction force 322 caused upon on the gas flow path 320 likewise ceases, and the gravity-assisted valve 180 will move from the second position to the first position due to the gravitational force of valve member 189, and the expulsion force, if any, of the gas 20 or fluid 10 attempting to leave the vial 110 through the gas lumen 164. When the gravity-assisted valve 180 is in the first position, the first port 181 will be blocked and any reflux gas 20 or fluid 10 will accumulate in the elongated valve cavity 184.

The present disclosure is provided to enable any person skilled in the art to practice the various aspects described herein. The disclosure provides various examples of the subject technology, and the subject technology is not limited to these examples. Various modifications to these aspects will be readily apparent to those skilled in the art, and the generic principles defined herein may be applied to other aspects.

A reference to an element in the singular is not intended to mean "one and only one" unless specifically so stated, but rather "one or more." Unless specifically stated otherwise, the term "some" refers to one or more. Pronouns in the masculine (e.g., his) include the feminine and neuter gender (e.g., her and its) and vice versa. Headings and subheadings, if any, are used for convenience only and do not limit the invention.

The word "exemplary" is used herein to mean "serving as an example or illustration." Any aspect or design described herein as "exemplary" is not necessarily to be construed as preferred or advantageous over other aspects or designs. In one aspect, various alternative configurations and operations described herein may be considered to be at least equivalent.

A phrase such as an "aspect" does not imply that such aspect is essential to the subject technology or that such aspect applies to all configurations of the subject technology. A disclosure relating to an aspect may apply to all configurations, or one or more configurations. An aspect may provide one or more examples. A phrase such as an aspect may refer to one or more aspects and vice versa. A phrase such as an "embodiment" does not imply that such embodiment is essential to the subject technology or that such embodiment applies to all configurations of the subject technology. A disclosure relating to an embodiment may apply to all embodiments, or one or more embodiments. An embodiment may provide one or more examples. A phrase such an embodiment may refer to one or more embodiments and vice versa. A phrase such as a "configuration" does not imply that such configuration is essential to the subject technology or that such configuration applies to all configurations of the subject technology. A disclosure relating to a configuration may apply to all configurations, or one or more configurations. A configuration may provide one or more examples. A phrase such a configuration may refer to one or more configurations and vice versa.

In one aspect, unless otherwise stated, all measurements, values, ratings, positions, magnitudes, sizes, and other specifications that are set forth in this specification, including in the claims that follow, are approximate, not exact. In one aspect, they are intended to have a reasonable range that is consistent with the functions to which they relate and with what is customary in the art to which they pertain.

In one aspect, the term "coupled" or the like may refer to being directly coupled. In another aspect, the term "coupled" or the like may refer to being indirectly coupled.

Terms such as "top," "bottom," "front," "rear" and the like if used in this disclosure should be understood as referring to an arbitrary frame of reference, rather than to the ordinary gravitational frame of reference. Thus, a top surface, a bottom surface, a front surface, and a rear surface may extend upwardly, downwardly, diagonally, or horizontally in a gravitational frame of reference.

Various items may be arranged differently (e.g., arranged in a different order, or partitioned in a different way) all without departing from the scope of the subject technology.

All structural and functional equivalents to the elements of the various aspects described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed under the provisions of 35 U.S.C. §112, sixth paragraph, unless the element is expressly recited using the phrase "means for" or, in the case of a method claim, the element is recited using the phrase "step for." Furthermore, to the extent that the term "include," "have," or the like is used, such term is intended to be inclusive in a manner similar to the term "comprise" as "comprise" is interpreted when employed as a transitional word in a claim.

The Title, Background, Summary, Brief Description of the Drawings and Abstract of the disclosure are hereby incorporated into the disclosure and are provided as illustrative examples of the disclosure, not as restrictive descriptions. It is submitted with the understanding that they will not be used to limit the scope or meaning of the claims. In addition, in the Detailed Description, it can be seen that the description provides illustrative examples and the various features are grouped together in various embodiments for the purpose of streamlining the disclosure. This method of disclosure is not to be interpreted as reflecting an intention that the claimed subject matter requires more features than are expressly recited in each claim. Rather, as the following claims reflect, inventive subject matter lies in less than all features of a single disclosed configuration or operation. The following claims are hereby incorporated into the Detailed Description, with each claim standing on its own as a separately claimed subject matter.

The claims are not intended to be limited to the aspects described herein, but is to be accorded the full scope consistent with the language claims and to encompass all legal equivalents. Notwithstanding, none of the claims are intended to embrace subject matter that fails to satisfy the requirement of 35 U.S.C. §101, 102, or 103, nor should they be interpreted in such a way.

What is claimed is:

1. A vial access cap comprising:

a connector having an opening for providing access to a fluid pathway;

a canella extending into an interior of a vial, the canella having a fluid lumen operatively coupled to the fluid pathway and a gas lumen;

a gravity-assisted valve comprising a valve body defining an elongated valve cavity, a first port, a second port operatively coupled to the gas lumen, and a valve member movable between a sealable end of the elongated valve cavity proximal to the first port and a non-sealable end of the elongated valve cavity proximal to the second port; and a gas pathway extending from an interstitial space of the connector to the first port and from the second port to an interior volume of the vial.

2. The vial access cap of claim 1, wherein the opening of the connector further provides sealable access to the gas pathway, and the first port of the gravity-assisted valve is operatively coupled to the gas pathway.

3. The vial access cap of claim 1, wherein the valve member comprises a substantially spherical element.

4. The vial access cap of claim 1, wherein the connector defines a longitudinal axis, and both the valve body and the canella are generally aligned in parallel with the longitudinal axis.

5. The vial access cap of claim 1, wherein the elongated valve cavity includes an interior wall having one or more longitudinally extending channels.

6. The vial access cap of claim 5, wherein the elongated valve cavity further includes an interior wall disposed on the non-sealable end having one or more laterally extending channels that are orthogonally aligned with respect to the one or more longitudinally extending channels.

7. The vial access cap of claim 2, wherein one or more filters are disposed within the gas pathway.

8. The vial access cap of claim 2, wherein a portion of the gas pathway includes an interstitial space of the connector.

9. The vial access cap of claim 8, wherein the gravity-assisted valve is configured to allow bidirectional gaseous communications between the gas lumen and the interstitial space of the connector when the vial access cap is oriented with the opening of the connector pointing in a generally upward direction.

10. The vial access cap of claim 8, wherein the gravity-assisted valve is configured to allow gaseous communications from the interstitial space of the connector to the gas lumen when the vial access cap is oriented with the opening of the connector pointing in a generally downward direction.

11. The vial access cap of claim 8, wherein the gravity-assisted valve is configured to prohibit gaseous communications from the gas lumen to the interstitial space of the connector when the vial access cap is oriented with the opening of the connector pointing in a generally downward direction.

12. A syringe comprising:

a connector body section defining a longitudinal axis and comprising, a tip portion for fluid ingress and egress; and a gravity-assisted valve comprising a valve body defining an elongated valve cavity generally aligned with the longitudinal axis, a first port operatively coupled to the tip portion, a second port, and a valve member movable between a sealable end of the elongated valve cavity proximal to the first port and a non-sealable end of the elongated valve cavity proximal to the second port; and a barrel section generally aligned with the longitudinal axis and slidably engaged with a plunger, the barrel section defining a fluid reservoir within a volume of the barrel section controllable by an end of the plunger proximal the connector body section, the fluid reservoir operatively coupled to the second port of the gravity-assisted valve, wherein the sealable end of the elongated valve cavity is proximal to the fluid reservoir and the non-sealable end is distal to the fluid reservoir.

13. The syringe of claim 12, wherein the gravity-assisted valve is configured to allow bidirectional fluid communications between the tip portion and the fluid reservoir when the syringe is oriented with the tip portion pointing in a generally downward direction.

14. The syringe of claim 12, wherein the gravity-assisted valve is configured to allow fluid communication from the tip portion to the fluid reservoir when the syringe is oriented with the tip portion pointing in a generally upward direction.

15. The syringe of claim 12, wherein the gravity-assisted valve is configured to prohibit fluid communication from the fluid reservoir to the tip portion when the syringe is oriented with the tip portion pointing in a generally upward direction.

16. The syringe of claim 12, further comprising a gas pathway extending from an interstitial space of the connector body section to an interior volume of the plunger defining a gas reservoir.

17. The syringe of claim 12, wherein the tip portion is non-tapered and configured for sealed engagement with a female luer fitting.

18. A system for providing fluid communications, the system comprising:

a vial access cap affixed to a vial, the vial access cap comprising, a connector having an opening for providing access to a fluid pathway and sealable access to a gas pathway;

a canella extending into an interior of a vial, the canella having a fluid lumen operatively coupled to the fluid pathway and a gas lumen; and a first gravity-assisted valve comprising a first valve body defining a first elongated valve cavity, a first port of the first gravity-assisted valve operatively coupled to the gas pathway, a second port of the first gravity-assisted valve operatively coupled to the gas lumen, and a first valve member movable between a sealable end of the first elongated valve cavity proximal to the first port of the first gravity-assisted valve and a non-sealable end of the first elongated valve cavity proximal to the second port of the first gravity-assisted valve; and a syringe comprising, a connector body section defining a longitudinal axis and comprising, a tip portion for fluid ingress and egress; and a second gravity-assisted valve comprising a second valve body defining a second elongated valve cavity generally aligned with the longitudinal axis, a first port of the second gravity-assisted valve operatively coupled to the tip portion, a second port of the second gravity-assisted valve, and a second valve member movable between a sealable end of the second elongated valve cavity proximal to the first port of the second gravity-assisted valve and a non-sealable end of the second elongated valve cavity proximal to the second port of the second gravity-assisted valve; and a barrel section generally aligned with the longitudinal axis and slidably engaged with a plunger, the barrel section defining a fluid reservoir within a volume of the barrel section controllable by an end of the plunger proximal the connector body section, the fluid reservoir operatively coupled to the second port of the second gravity-assisted valve, wherein the tip portion of the syringe is removably coupled to the opening of the vial access cap, and the fluid pathway and the gas pathway of the vial access cap are operatively coupled to a fluid pathway and a gas pathway of the syringe.

19. The system of claim 18, wherein the gas pathway of the vial access cap and the gas pathway of the syringe are configured for one of a venting or a non-venting arrangement.

* * * * *